United States Patent

Syré

[11] Patent Number: 5,892,157
[45] Date of Patent: Apr. 6, 1999

[54] APPARATUS FOR MEASURING THE FLEXURAL STIFFNESS OF MOVED LAMINAR-SHAPED MATERIAL

[75] Inventor: Hans-Richard Syré, Neuwied, Germany

[73] Assignee: Honeywell Inc., Minneapolis, Minn.

[21] Appl. No.: 931,382

[22] Filed: Sep. 16, 1997

[30] Foreign Application Priority Data

Sep. 17, 1996 [DE] Germany .................. 196 37 808.7

[51] Int. Cl.$^6$ .................................................. G01N 3/32
[52] U.S. Cl. .............................................. 73/812; 73/849
[58] Field of Search ....................... 73/812, 849, 818, 73/826

[56] References Cited

U.S. PATENT DOCUMENTS

| | | | |
|---|---|---|---|
| 3,196,672 | 7/1965 | Keller | 73/812 |
| 4,347,736 | 9/1982 | Desai et al. | 73/73 |
| 4,589,288 | 5/1986 | Porter et al. | 73/852 |
| 5,503,024 | 4/1996 | Bechtel | 73/849 |
| 5,507,189 | 4/1996 | Kim et al. | 73/838 |
| 5,574,227 | 11/1996 | Allan | 73/849 |

*Primary Examiner*—Max H. Noori
*Attorney, Agent, or Firm*—Anthony Miologos

[57] ABSTRACT

An apparatus for measuring the flexural stiffness of a moving laminar-shaped material web is disclosed that guides the material web over two stationary guide rollers and a deflecting roller. The deflecting roller rides on the material web and deflects the material web for a predetermined distance. A force-measuring device attached to the deflecting roller measures the force exerted by the material web. An actuator movably attached to the force-measuring device is actuated periodically to move the deflecting roller into the material web whereby the force related to the additional periodic deflection is measured by the force-measuring device and evaluated to determine the flexural stiffness of the material web. In a second embodiment of the present invention, the actuator is not used and the deflecting roller includes an eccentric cross-section which imparts on the material web a periodic deflection of the web.

10 Claims, 4 Drawing Sheets

APPARATUS FOR MEASURING THE FLEXURAL STIFFNESS OF MOVED LAMINAR-SHAPED MATERIAL

FIELD OF THE INVENTION

This invention relates generally to a measuring apparatus and more particularly to an apparatus for measuring the flexural stiffness of laminar-shaped material web as it is manufactured.

BACKGROUND OF INVENTION

In the manufacture of a sheet material, such as cardboard, the measuring of the flexural stiffness of the cardboard material is of critical importance to both end users and manufacturers. The flexural stiffness of the cardboard correlates directly to its strength and its strength determines the quality of the end product in which the cardboard material is used. Additionally, in the manufacturing process of this type of sheet material, it is advantageous to measure the sheet material's flexural stiffness during its manufacture in order to monitor and maintain a predetermined strength of the material and to intervene directly into the manufacturing process "on-line" at the first indication of a deviation from the desired strength. Present cardboard manufacturing methods employ a high-speed manufacturing process that manufactures cardboard in a continuous web at speeds of 500 meters/minute. Therefore, deviations from a quality standard must be recognized early and the manufacturing process adjusted or large amounts of undesirable material will be manufactured.

In a laboratory setting, a sample of cardboard material is tested as a transverse beam. The German Standard DIN53121 includes a two-point measuring method with a unilateral biasing and a load at the free end and a three-point measuring method that utilizes two supports that support the specimen to be measured from below with a force applied from above. This force is applied and increased until a selected bending is achieved. The force is measured and its value inserted into a formula to calculate the specific flexural stiffness of the material under test.

In a continuous manufacturing process the material web under test is moved through a similar apparatus. The difference with respect to the laboratory method is that the material under test is supported by two rollers. The force acting from above also is applied to the material under test by means of a roller. This force is measured by a load cell, implemented by an arrangement of inductive or capacitive strain gauges, by piezoceramic elements, or by accordingly-shaped semiconductor elements. The load cell is mounted at a stationary support, and the force measured by the load cell is converted into an analog electrical signal, which is evaluated by associated evaluation electronics. The deflection of the material web is done by means of an actuator which may be positioned between the stationary support and the load cell or between the load cell and the roller, respectively.

However, during the continuous manufacturing process the material web is also under an additional force imparted by the tension of the material web. When the signal of the load cell alone is evaluated, it cannot be recognized whether the measured force is due to the web tension, the flexural stiffness, or to both values.

FIG. 6, of European Patent 0 541 518 B1, shows an apparatus for determining the strength of sheet materials. The material web is guided over a circular-shaped supporting device, and a deflection device arranged in the middle of the support device deflects the material web. A load cell measures the force exerted by the material web onto the support device. However, in order to correctly calculate the flexural stiffness, other values, including web tension, must be inputted into a computer to correct the value read by the load cell.

SUMMARY OF THE INVENTION

Therefore, there is provided by the present invention an apparatus for measuring the flexural stiffness of a moving laminar-shaped material web comprised of at least first and second supporting devices spaced apart from each other and arranged to support and convey thereon the material web. A deflecting device located between the first and second supporting devices and on an opposite surface of the material web is arranged to deflect the material web by a predetermined amount. The apparatus of the present invention further includes a force-measuring device that measures the deflection force conveyed to the material web by the deflecting device. The flexural stiffness of the moving material web is ascertained by periodically additionally deflecting the material web by periodic deflecting means.

In a first embodiment, the periodic deflecting means is comprised of an actuator that is arranged to periodically additionally deflect the deflecting device into the material web. In a second embodiment, various devices having an eccentric cross-section are substituted for the actuator and used to provide the additional periodic deflection.

An evaluation means connected to the force-measuring device correlates the resultant force produced by extracting the force due to the periodic additional deflection from the deflection force to the flexural stiffness of the material web. A signal representing the flexural stiffness of the material web can then be read from the evaluation device by an automated process control system or other control or display system that is monitoring and/or controlling the manufacture of the sheet material.

It is, therefore, an object of the present invention to provide an apparatus which allows in a simple and expedient manner the evaluation of the flexural stiffness of a moving laminar-shaped material web.

These and other objects of the present invention will become more apparent when taken in conjunction with the following description and attached drawings and which drawings form a part of the present invention.

BRIEF DESCRIPTION OF THE DRAWINGS

FIG. 6b is a vector diagram of the forces shown in FIG. 6a.

DETAILED DESCRIPTION OF THE INVENTION

Figure 1:
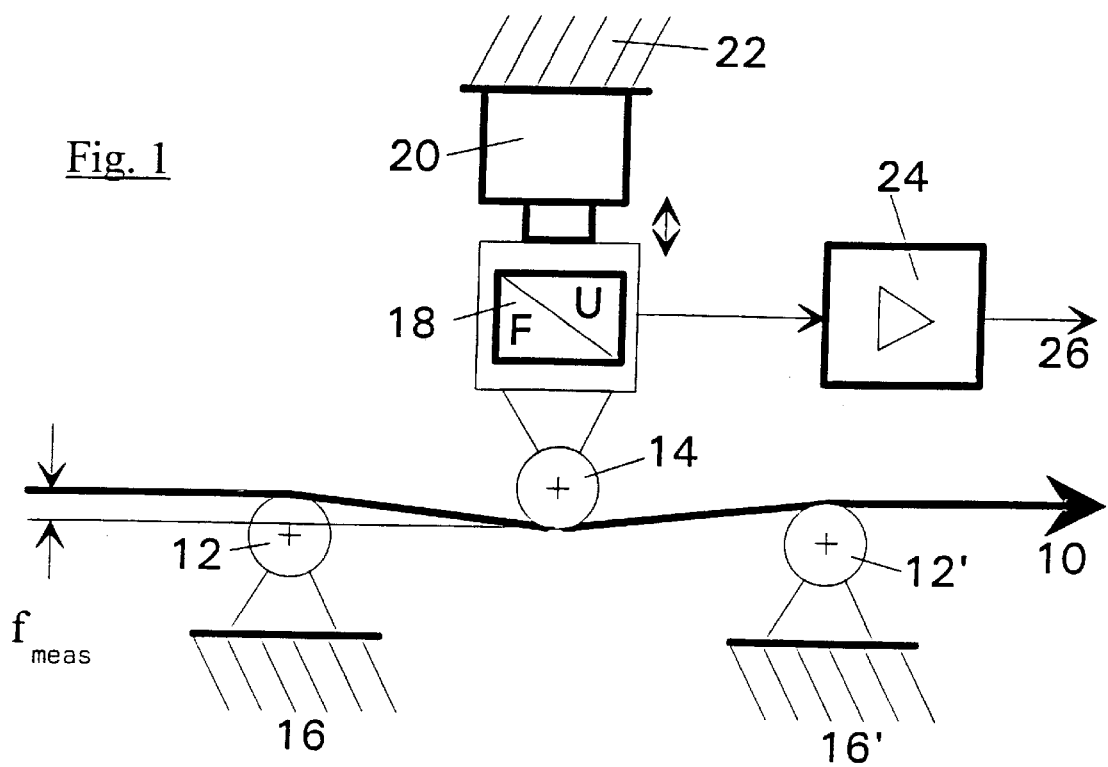
FIG. 1 is a representation of the apparatus for measuring flexural stiffness in accordance to the present invention positioned longitudinally to the material web.

Turning to FIG. 1, a web-shaped material under test 10, whose flexural stiffness is to be determined, is guided into the apparatus of the present invention via supporting devices in the form of guide rollers 12 and 12'. Midway between the guide rollers 12 and 12' there is provided a deflection device comprised of a deflecting roller 14, fixedly mounted to a force-measuring device such as a dynamometer or load cell 18. The force-measuring device 18 is attached to the movable arm of an actuator 20. Guide rollers 12 and 12' are directly supported by stationary supports 16, 16'. Actuator 20 is supported by a stationary support 22.

The material web 10 is normally passed at high speed over guide rollers 12 and 12' in the direction shown by the arrow. The deflecting roller 14 rides on the material web 10 and deflects the material web for a predetermined distance. Periodically, actuator 20 is activated, deflecting roller 14 an additional distance onto the material web 10. The material web 10 is thus deflected periodically for an additional predetermined distance The forces acting on the deflecting roller 14, in response to the periodic deflection of the web material 10, is sensed and measured by force-measuring device 18 and output to an electronic evaluation device 24. Electronic evaluation device 24 receives the signal associated with the periodic deflection of the web material and extracts from the total signal the signal which is related to the periodic deflection, thereby applying at output 26 a signal representative of the flexural stiffness of the material web 10.

The signal at output 26 from the electronic evaluation device 24 can be transmitted as data to a process control system that can retrieve, translate, store, and/or display the data. Additionally, the data so retrieved can be used by the process control system to ascertain if a deviation from a quality standard has occurred that requires an adjustment to the manufacturing process.

Actuator 20 may be one of a plurality of mechanical devices known to those skilled in the art, that can be used to achieve a movement in the direction of the material web 10 under test, such as eccentric disc/push rod or piston rod/crank handle arrangements. Still other types of mechanical devices that can be effectively used as actuators include pneumatic short stroke cylinders, electromechanical actuators i.e. solenoid/push-rod arrangements or piezo actuators.

Figure 2:
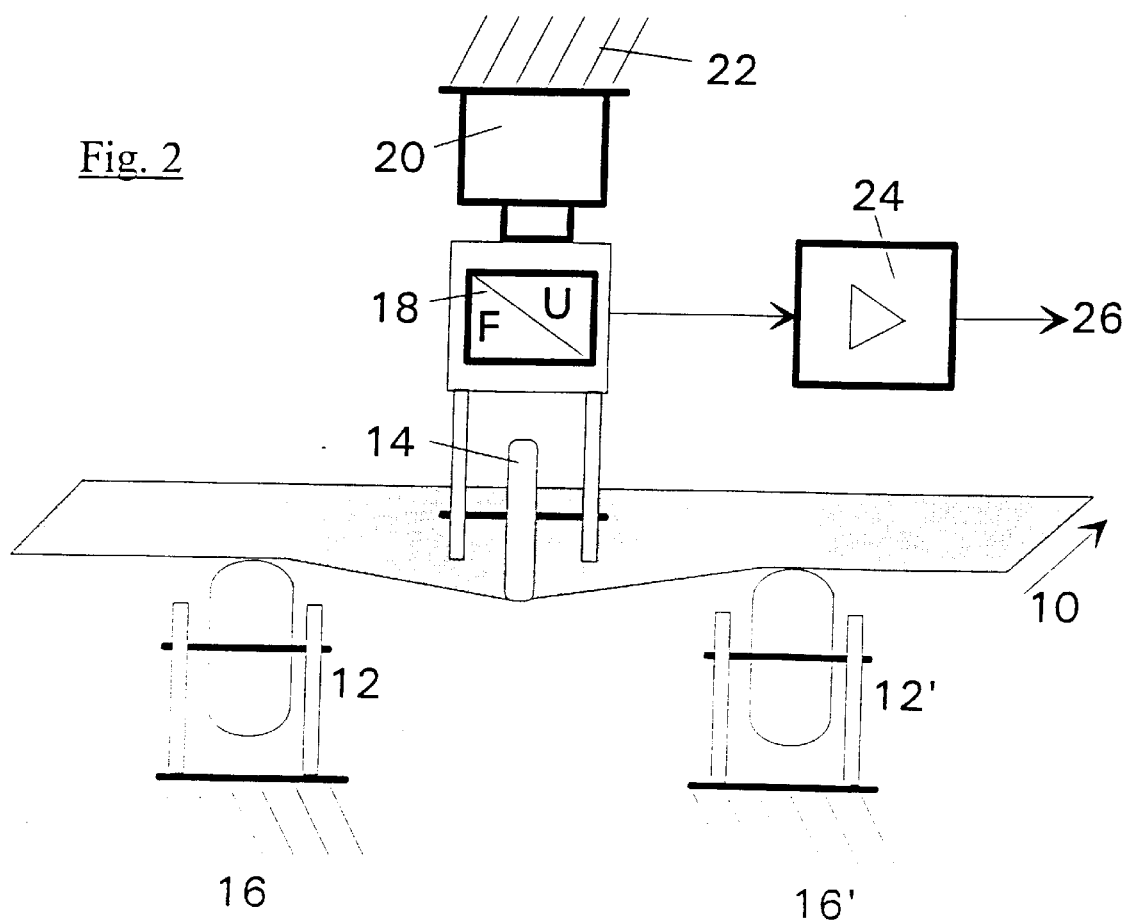
FIG. 2 is a representation of the apparatus for measuring flexural stiffness in accordance to the present invention positioned transversely to the material web.

Turning now to FIG. 2, an apparatus corresponding with respect to the components and operation shown in FIG. 1, is illustrated. The material web under test 10 is moved in the direction shown by the arrow; and the guide rollers 12, 12', and deflecting roller 14 are arranged transverse to the material web 10 under test. In situations were the material web under test shows a high anisotropically distributed density, the flexural stiffness is measured in the longitudinal direction, as shown in FIG. 1, as well as in the transverse direction, as shown by FIG. 2.

Figure 3:
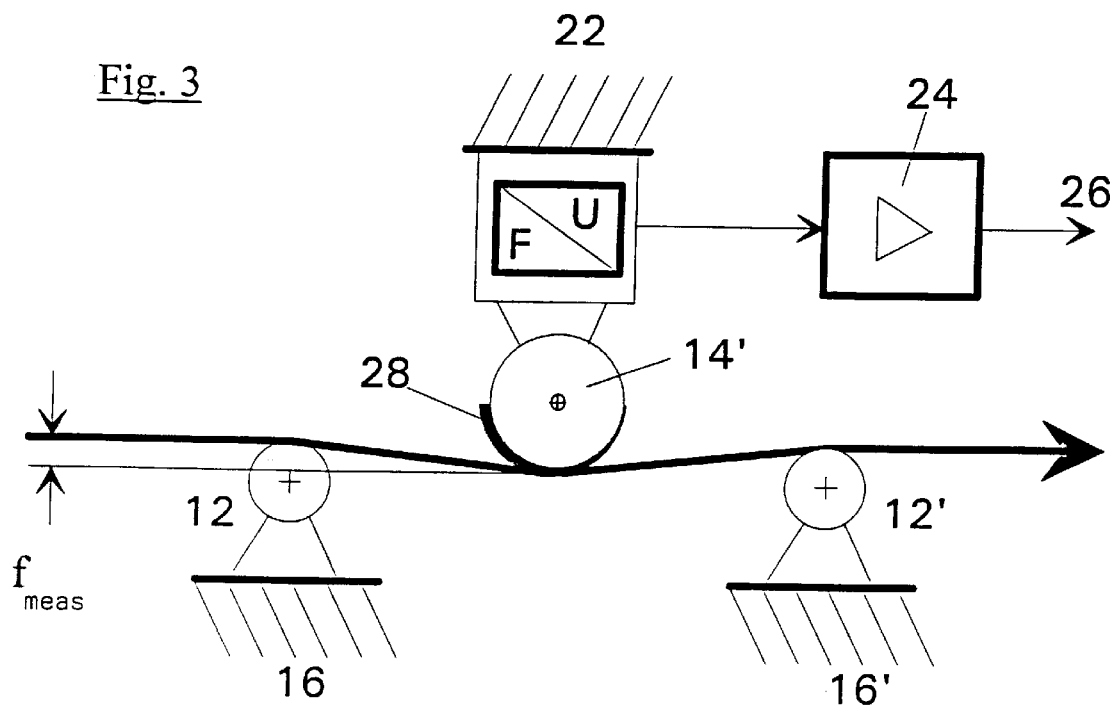
FIG. 3 is a representation of a second embodiment of the apparatus for measuring flexural stiffness in accordance to the present invention.

A second embodiment of the present invention is illustrated in FIG. 3. The apparatus of FIG. 3 essentially corresponds to the device of FIG. 1 with the exception that the actuator 20 is not present and a periodic deflecting device is used to impart a downward pressure on the material web 10. As can be seen, deflecting roller 14' is provided with a surface coating 28 which extends over a portion of the perimeter of the roller 14'. As the deflecting roller 14' is driven by the friction of material web 10, the surface coating 28 imparts a periodic downward deflection to the material web 10.

Figure 4:
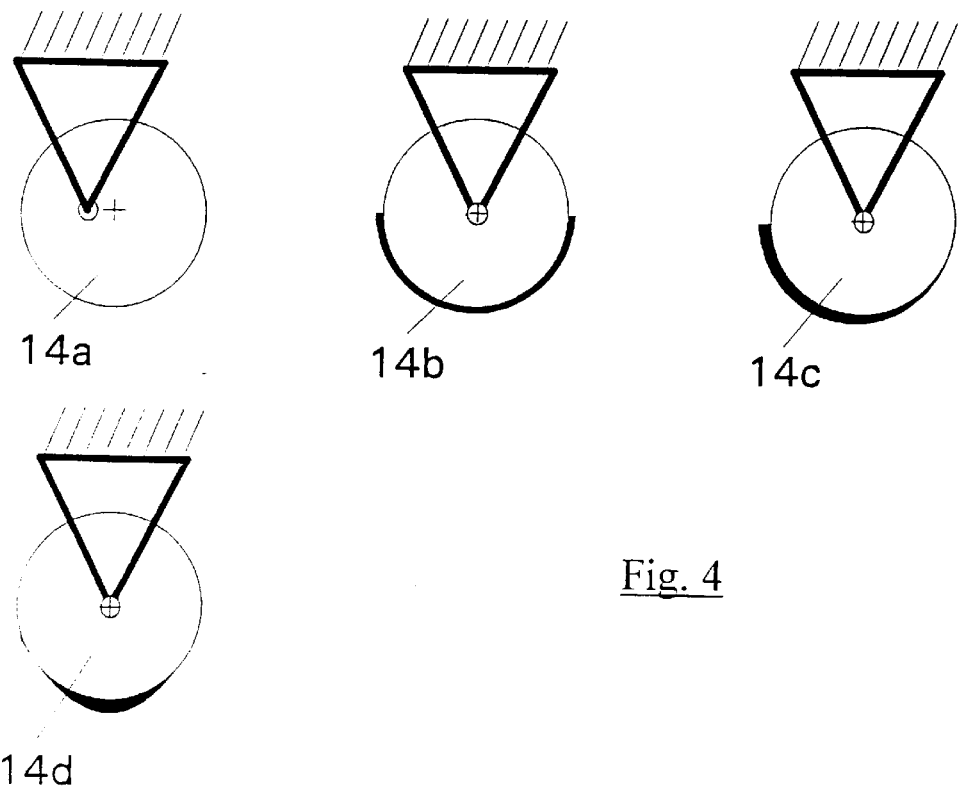
FIG. 4 are representations of alternative periodic deflecting devices used to advantage with the second embodiment of the present invention.

Other types of periodic deflecting devices that may be used to advantage with the apparatus of FIG. 3 are illustrated in FIG. 4. A simple periodic deflecting device can be implemented by the off-center mounting of the deflecting roller, as shown by deflecting roller 14a. The off-center mounting of deflecting roller 14' produces a sinusoidal change of the deflection of the material web 10. Deflecting roller 14b has a coating applied to over half of its perimeter, thereby providing a slightly increased radius where the coating is applied. Deflecting roller 14c is center mounted but has a surface coating in form of an Archimedes spiral. Finally, the deflecting roller may be provided with a coating of random curvature as shown by deflecting roller 14d of a type that can produce force patterns which can be well analyzed and calculated by analytical or numerical methods.

It will be appreciated by those skilled in the art that other forms of periodic deflecting devices can be used to perform the function of deflecting the material web for an established distance and that the deflecting rollers illustrated by 14a–14d are only a small example of the devices that can be used and, therefore, the present invention is not limited thereto.

Figure 5:
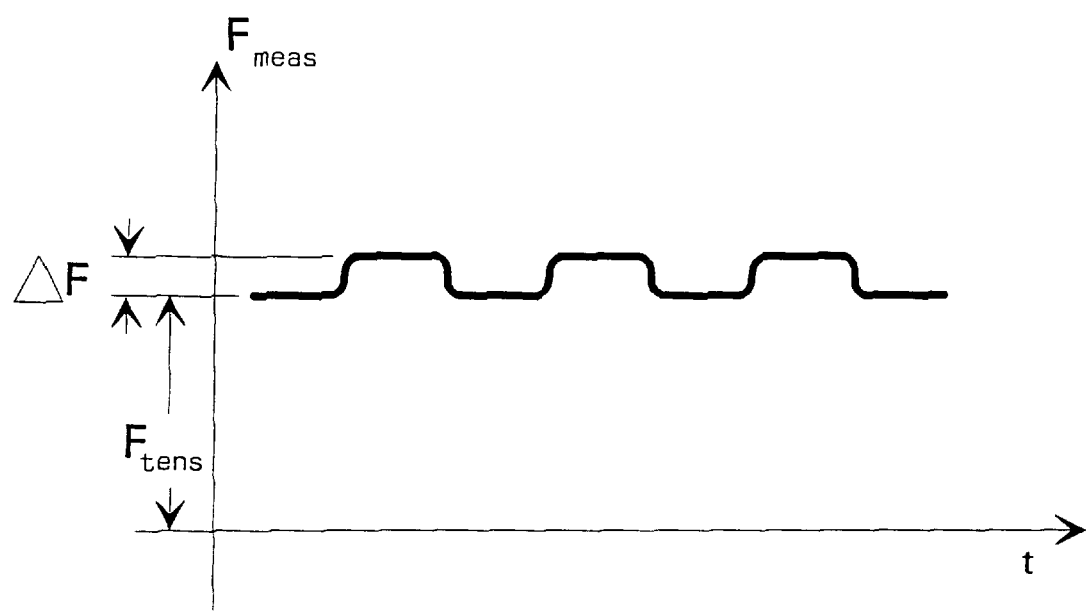
FIG. 5 is a signal diagram of the measured force as a function of time when using one of the periodic deflecting devices of FIG. 4.

FIG. 5 shows a diagram for the measured force ($F_{meas}$) as a function of time (t) when a deflecting roller 14' is used that has an eccentric cross section showing a radius increase over half of its perimeter, as those shown in FIG. 4. Force $\Delta F$ is superimposed on the constantly acting tension ($F_{tens}$) which is produced by the enlarged sector of the guide roller 14'. By evaluating the $\Delta F$ force modulated onto the constant acting tension ($F_{tens}$), the flexural stiffness of the material may be ascertained.

Figure 6A:
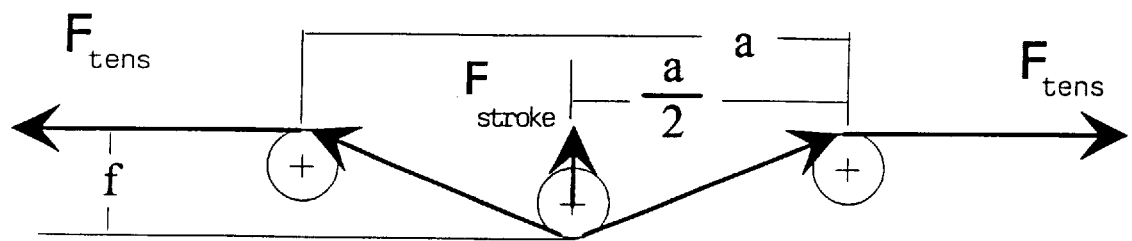
FIG. 6a is a force diagram of the forces normally imparted by the material web.
Figure 6B:
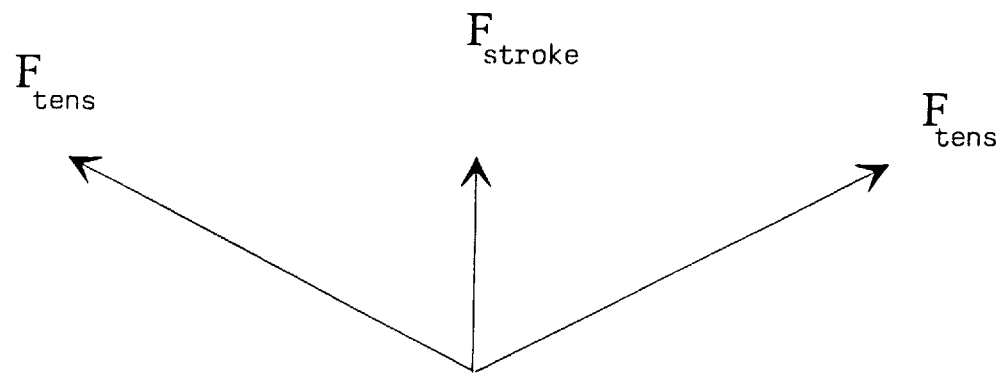
Figure 6C:
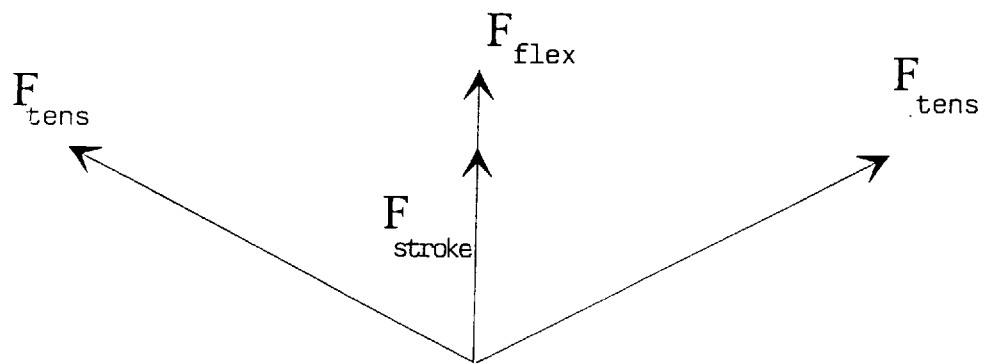
FIG. 6c is a vector diagram of the forces imparted by the additional deflection of the material web by the periodic deflecting devices of the present invention.

With reference to FIG. 6a, 6b and 6c vector diagrams of the forces acting on the material web are illustrated. Specifically, FIG. 6a shows the forces acting on the device of the present invention and material web in accordance to the apparatus of FIG. 1 and FIG. 2. As can be appreciated by those skilled in the art and as can be seen in FIG. 6b, in the case of a web material without flexural stiffness, the stroke force ($F_{stroke}$) can be ascertained graphically as well as by computational methods when the tension ($F_{tens}$) is known.

However, in the case where the web material under test has a flexural stiffness in addition to the stroke force ($F_{stroke}$), a flexural force ($F_{flex}$) appears as shown in FIG. 6c. Both forces ($F_{stroke}$) and ($F_{flex}$) act in the same direction and are not measurable as individual forces. In accordance to the present invention, the force attributable to the flexural stiffness can be determined by periodically changing the submergence or the distance that the deflecting rollers 14, 14' deflect material web 10. If the distance of submergence or periodic deflection is small, then the total path length change is negligible and the change of the tension ($F_{tens}$) can be disregarded. The change of the force applied by the deflecting rollers 14, 14', and measured by the force-measuring-device 18, is due only to the flexural stiffness of the material web being tested.

The present invention has been described with particular reference to the preferred embodiments thereof. It will be obvious that various changes and modifications may be made therein without departing from the spirit and scope of the invention as defined in the appended claims.

What is claimed is:

1. An apparatus for measuring the flexural stiffness of a moving laminar-shaped material web comprising:

at least first and second supporting devices spaced apart from each other and arranged to support and convey thereon said material web;

a deflecting device located between said first and second supporting devices, said deflecting device deflecting by a predetermined amount said material web;

a force-measuring device for measuring the deflection force conveyed to said material web by said deflecting device;

periodic deflecting means arranged to additionally deflect periodically said material web beyond the predetermined amount of deflection imparted by said deflecting device; and evaluation means for correlating a resultant force to the flexural stiffness of the material web, measured by the force-measuring device and which is due to the additional periodic deflection.

2. The apparatus as claimed in claim 1 wherein said evaluation means comprises an electronic device arranged to receive from said force-measuring device signals representing said deflection force conveyed to said material web by said deflecting device and signals representing the additional periodic deflection force conveyed to the said material web by said periodic deflecting means whereby said evaluation device extracts the additional periodic deflection force from the deflection force and produces an output signal representative of the flexural stiffness of the material web.

3. The apparatus as claimed in claim 2 wherein said apparatus further includes first, second, and third stationary supports and said material web includes first and second surfaces and said first and said second supporting devices are comprised of first and second guide rollers, and said first and second guide rollers are attached to said first and second stationary supports respectively, with each guide roller communicating with said first surface of said material web.

4. The apparatus as claimed in claim 3 wherein said force-measuring device is attached to said third stationary support and said deflecting device includes a deflecting roller mounted to said force-measuring device with said deflecting roller communicating with said material web second surface whereby said deflecting roller is driven by the moving material web.

5. The apparatus as claimed in claim 4 wherein said first and second rollers and said deflecting roller are arranged in a longitudinal direction of said material web.

6. The apparatus as claimed in claim 4 wherein said first and second rollers and said deflecting roller are arranged in a transverse direction side-by-side to said material web.

7. The apparatus as claimed in claim 4 wherein said first and second rollers and said deflecting roller are arranged in a longitudinal direction as well as a in transverse direction of said material web.

8. The apparatus as claimed in claim 7 wherein said periodic deflecting means comprises an actuator mounted between said third stationary support and said force-measuring device, whereby responsive to said actuator said deflecting roller produces said additional periodic deflection of said material web.

9. The apparatus as claimed in claim 7 wherein said periodic deflecting means comprises said deflecting roller mounted to said force-measuring device eccentrically whereby responsive to said material web driving said deflecting roller, said deflecting roller produces said additional periodic deflection of said material web.

10. The apparatus as claimed in claim 9 wherein said deflecting roller includes a perimeter surface and said periodic deflecting means comprises a raised coating located over a portion of said perimeter surface whereby responsive to said material web driving said deflecting roller, said deflecting roller produces said additional periodic deflection of said material web.

* * * * *